(12) United States Patent
Mirzaians (10) Patent No.: US 11,076,684 B2
(45) Date of Patent: Aug. 3, 2021

(54) EAR PROTECTION APPARATUS

(71) Applicant: Syuzan Mirzaians, Glendale, CA (US)

(72) Inventor: Syuzan Mirzaians, Glendale, CA (US)

(73) Assignee: Syuzan Mirzaians, Glendale, CA (US)

(*) Notice: Subject to any disclaimer, the term of this patent is extended or adjusted under 35 U.S.C. 154(b) by 32 days.

(21) Appl. No.: 16/565,349

(22) Filed: Sep. 9, 2019

(65) Prior Publication Data

US 2020/0077768 A1 Mar. 12, 2020

Related U.S. Application Data

(60) Provisional application No. 62/729,683, filed on Sep. 11, 2018.

(51) Int. Cl.
*A45D 44/12* (2006.01)
*A61F 11/14* (2006.01)

(52) U.S. Cl.
CPC .............. *A45D 44/12* (2013.01); *A61F 11/14* (2013.01)

(58) Field of Classification Search
CPC .......... A45D 44/12; A61F 11/14; A61F 11/06; A61F 11/12; A61F 11/00; A42B 3/16
See application file for complete search history.

(56) References Cited

U.S. PATENT DOCUMENTS

| | | |
|---|---|---|
| 1,326,875 A | 12/1919 | Miller |
| 2,118,273 A * | 5/1938 | Smith ................... A45D 44/12 2/174 |
| 2,149,210 A | 2/1939 | Fairchild |
| 2,446,122 A | 7/1948 | Bills |
| 2,769,980 A | 11/1956 | Fleischer |
| 3,167,785 A | 2/1965 | Uhl |
| 3,235,882 A | 2/1966 | Coleman |
| 4,616,643 A | 10/1986 | Jung |
| 5,023,954 A | 6/1991 | Lyons |
| 5,675,840 A | 10/1997 | Clavelle |
| 5,718,001 A * | 2/1998 | Wright ................... A45D 44/12 128/864 |
| 5,867,834 A * | 2/1999 | Simpson ................ A45D 44/12 2/171 |

(Continued)

OTHER PUBLICATIONS

Acrylic Sleeve_Wiremasters.net_06-02-2017_Wayback Machine. pdf https://wiremasters.net/products/tubing/m390 Wayback Machine Internet Archive Jun. 2, 2017 (Year: 2017).*

(Continued)

*Primary Examiner* — Clinton T Ostrup
*Assistant Examiner* — Keith D Stephan-Giermek
(74) *Attorney, Agent, or Firm* — Cotman IP Law Group APLC (57) ABSTRACT

An ear protection apparatus includes a flexible ear guard assembly with an integrally formed ear protector on each end of a connecting band. The connecting band is configured to position each of the ear protectors in contact with an ear of a user. The ear protection apparatus further includes a support structure coupled to the top of the ear guard assembly for structural stiffness. The support structure is configured to be deformable or bendable into different shapes such that it can be folded behind the user's neck or head to cover each ear thus protecting it from heat and/or chemicals during hair styling. The ear protector may optionally include a pair of breathable ear cups.

6 Claims, 11 Drawing Sheets

(56) References Cited

U.S. PATENT DOCUMENTS

| | | | |
|---|---|---|---|
| 6,131,204 | A | 10/2000 | Otey |
| 6,298,493 | B1 | 10/2001 | Ambroise |
| 6,505,633 | B2 | 1/2003 | Mosely |
| 6,637,039 | B1 | 10/2003 | Manuel |
| 7,614,091 | B2 * | 11/2009 | LeGette .................. A61F 11/14 128/857 |
| 2001/0010727 | A1 * | 8/2001 | Urwyler ............... H04R 1/1033 381/384 |
| 2006/0015989 | A1 * | 1/2006 | Faussett ............... H04R 5/0335 2/423 |

OTHER PUBLICATIONS https://www.amazon.com/Hair-Dryer-Heat-Shield-Purple/dp/B00JBQ17QU/ref=sr_1_cc_2_a_it?s=aps&ie=UTF8&qid=1516619712&sr=1-2-catcorr&keywords=neck%2Bprotection%2Bfrom%2Bhair%2Bstyle&th=1.

https://www.amazon.com/Ear-Shields-Protectors-Slip-Pair/dp/B00VG149L8/ref=pd_bxgy_194_img_2?_encoding=UTF8&pd_rd_i=B00VG149L8&pd_rd_r=9KM3CCSW8JBKZPSQ4SGS&pd_rd_w=K2ewN&pd_rd_wg=YrFNX&psc=1&refRID=9KM3CCSW8JBKZPSQ4SGS.

* cited by examiner

Section A-A

FIG. 5F

Detail B

EAR PROTECTION APPARATUS

CROSS-REFERENCE TO RELATED APPLICATIONS

The present application claims the benefit of U.S. Provisional Application Ser. No. 62/729,683, filed on Sep. 11, 2018, specification of which is herein incorporated by reference for completeness of disclosure.

BACKGROUND OF THE INVENTION

Field of the Invention

Embodiments of the invention relates to the field of heat shields for shielding the ears of a person during styling. More specifically, the invention relates to protection apparatus for a user's ears from heat, dyes, etc. while hair styling.

Description of the Related Art

There exists a substantial industry devoted to treating and styling hair in order to alter the appearance of their hair. Typically, hair treatments are performed at hair salons or at home. Such treatments may involve altering the color of hair, for example in dying, highlighting or bleaching, or the modification of hair structure, for example in perming, curling or relaxing. During such treatments, heat cosmetology instruments, chemicals and styling products may be used.

Users typically wear gloves for hair treatments requiring the use of chemical products. The gloves protect against risk of skin irritation and injury to the hand. However, due to the proximity of the head hair to the ears, the gloves do not protect against the risk that such products may inadvertently contact the outer ear and/or enter the ear canal.

Hair treatment chemicals can be left on the hair to take effect for a short period of time or for a longer period of time, depending on the hair type and the application time used. However, even if the product is rinsed off relatively quickly, damage to the skin on the ear can occur if there has been contact between the product and that skin. This is a particular problem when the user has sensitive skin.

Users who dye their hair face the possibility that residual dye may remain on the skin if the dye is kept on for too long, or if the dye is not thoroughly washed away. The upper ear often comes into contact with dyes during the application process and, as a consequence, the skin at the top of the ear and/or on the back of the ear can easily become stained by the dye.

Hair heating appliances, such as hairdryers, curling tongues and straightening tongues, present a further risk to ears, as the fragile skin of ears is easy to burn when the hair is being styled and/or dressed. While heat generating cosmetology instruments are effective in styling hair, the excessive heat from these devices may burn or irritate the user's ear, for example. The excessive heat generated by some heat cosmetology instruments, such as a hooded hair dryer, for example, may cause hot air burns and discomfort to a user's ears.

To overcome the problems and limitations described above there is a need for the ear protection apparatus of the present invention.

BRIEF SUMMARY OF THE INVENTION

One or more embodiments of the invention are directed to an ear protection apparatus. The ear protection apparatus comprises a flexible ear guard assembly with an integrally formed ear protector on each end of a connecting band. The connecting band is configured to position each of the ear protectors in contact with an ear of a user. The ear protection apparatus further includes a support structure coupled to the top of the ear guard assembly to provide structural stiffness. The support structure is configured to be deformable or bendable into different shapes such that it can be folded behind the user's neck or head to cover each ear thus protecting it from heat and/or chemicals during hair styling.

In one or more embodiments, the ear guard assembly comprises a connecting band and an integrally formed ear protector on each end of the connecting band. The connecting band is configured to position each one of the ear protectors in contact with an ear of a user, the connecting band is further configured to be foldable behind the user's neck. The ear protector comprises a frame that is sized and shaped to substantially cover the ear of the user, the frame comprises an outer shell that defines an inner cavity, the inner cavity comprises a pocket that is sized and shaped to be slidably received over the user's ear to support the frame on top of the user's ear.

In one or more embodiments, the support structure comprises an acrylic overmold coupled to a metal wireframe via a plurality of adjustable legs. The metal wireframe could be made of steel or any other suitable metal.

In one or more embodiments, the support structure is removably coupleable to the ear guard assembly. The support structure is configured to be deformable to a shape around the back of the user's neck or head. The support structure comprises an acrylic overmold coupled to a metal wireframe embedded into the ear guard assembly.

In one or more embodiments, the ear guard assembly comprises a heat resilient material such as silicon.

In one or more embodiments, the ear protector may optionally include a pair of breathable ear cups.

In one or more embodiments, the outer shell further includes at least one opening to provide communication between the inner cavity and the exterior of the ear protector.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

The present invention comprising an apparatus for ear protection will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art would recognize that the steps or processes may be performed in a different order, and that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. It should be noted that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

One or more embodiments of the present invention will now be described with references to FIGS. 1-11.

Figure 1:
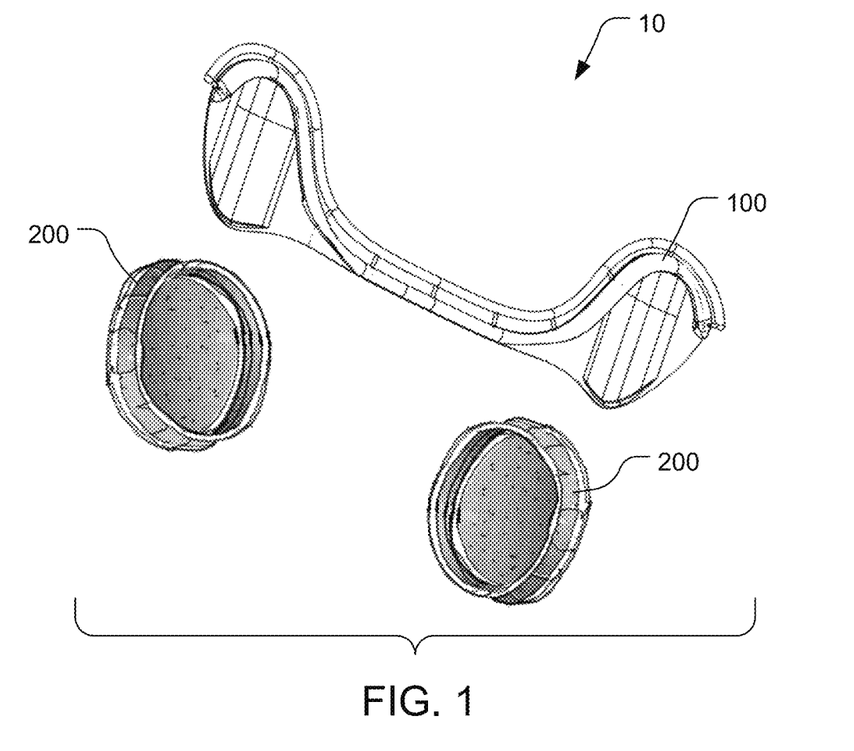
FIG. 1 is an illustration of the components of the ear protection apparatus in accordance with one or more embodiments of the present invention.
Figure 11:
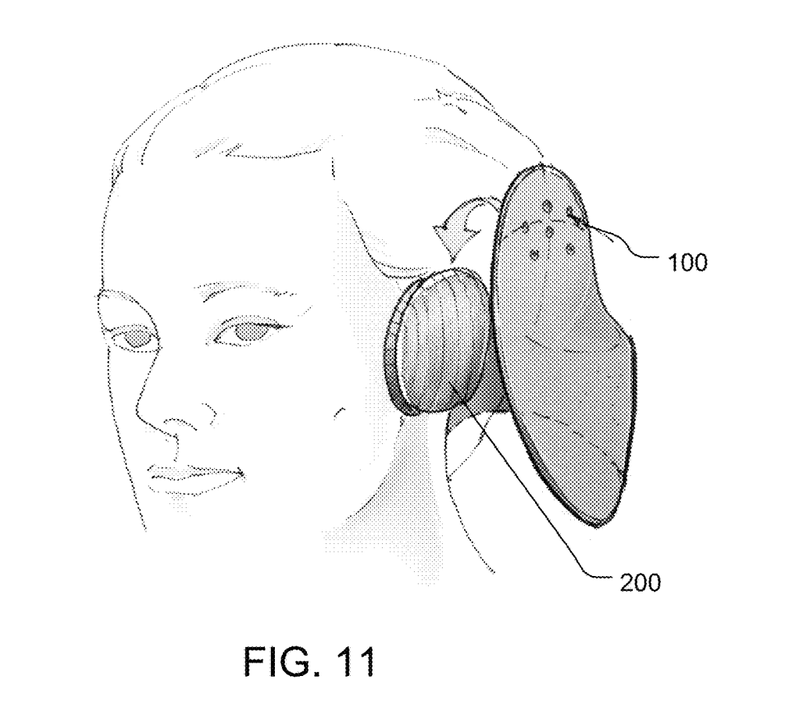
FIG. 11 is an illustration of application of the protective band of the ear protection apparatus over the ear cup on the wearer's ear.

One or more embodiments of the ear protection apparatus 10 comprises a heat resilient ear guard assembly 100 with an integrally formed ear protector on each end of a connecting band; and a pair of optional ear cups 200. Each ear cup 200 comprises soft breathable material and is configured to fit over a wearer's ear (See. FIG. 11).

Figure 2:
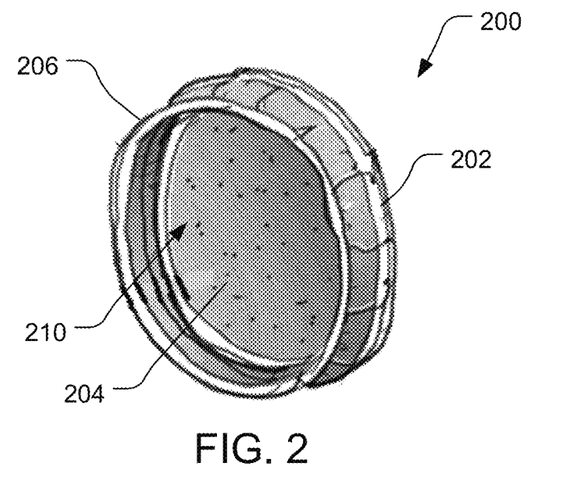
FIG. 2 is an illustration of an ear cup of the ear protection apparatus in accordance with one or more embodiments of the present invention.
Figure 3A:
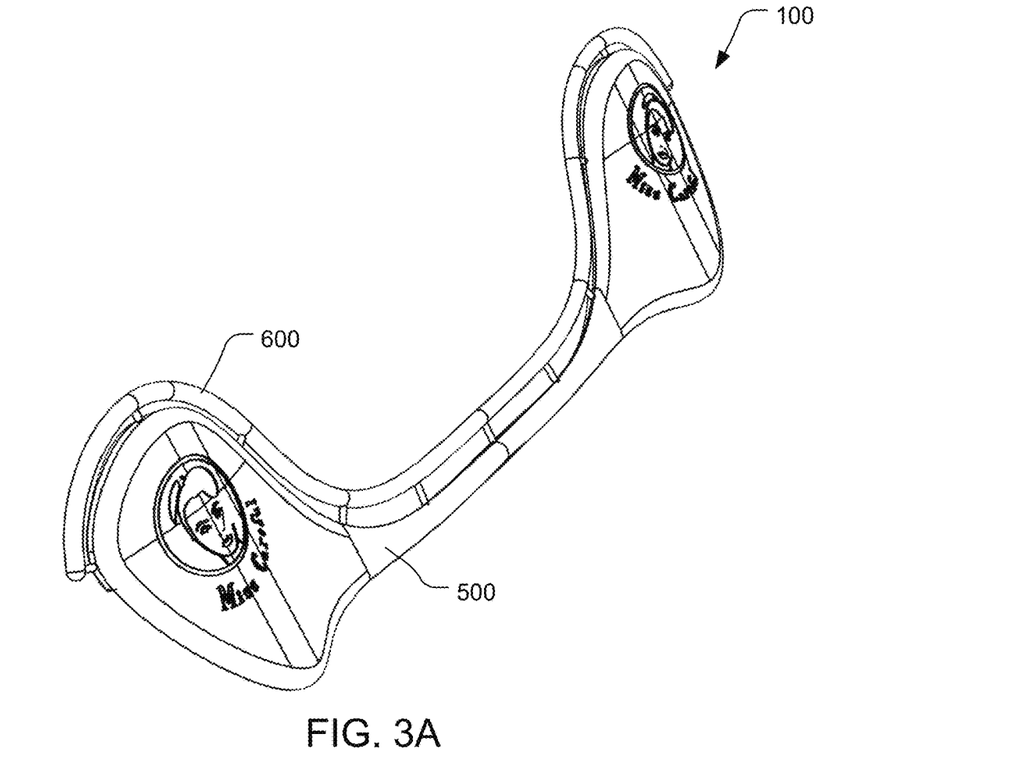
FIG. 3A is a front perspective view the ear guard assembly of the ear protection apparatus in accordance with one or more embodiments of the present invention.
Figure 3B:
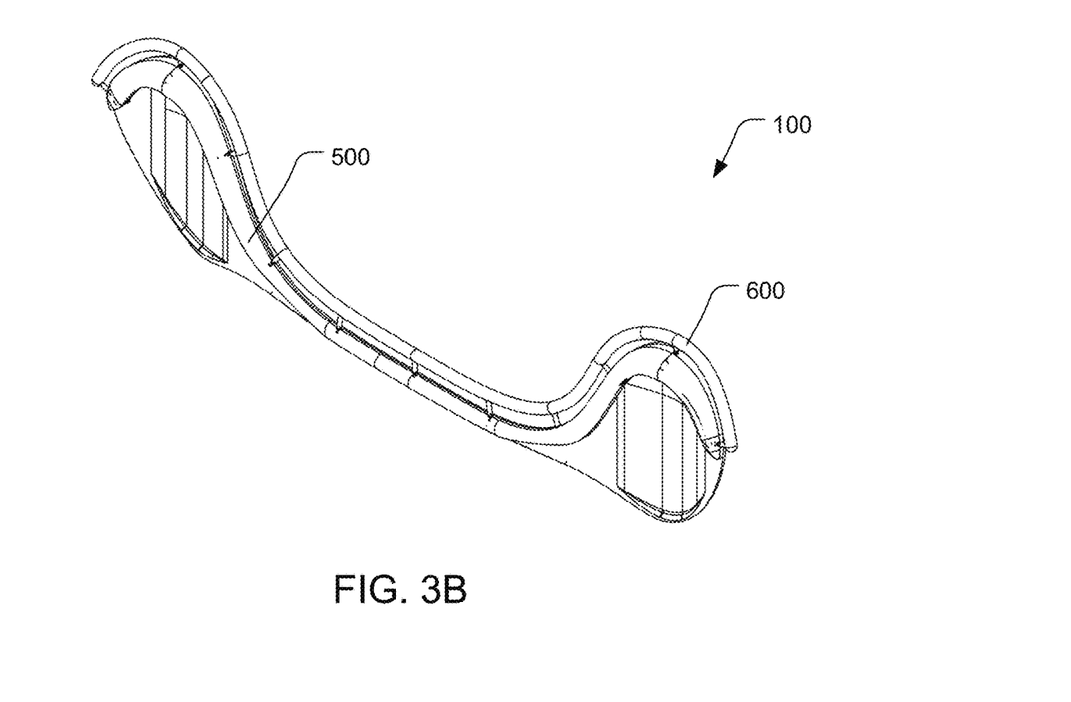
FIG. 3B is a back perspective view the ear guard assembly of the ear protection apparatus in accordance with one or more embodiments of the present invention.
Figure 3C:
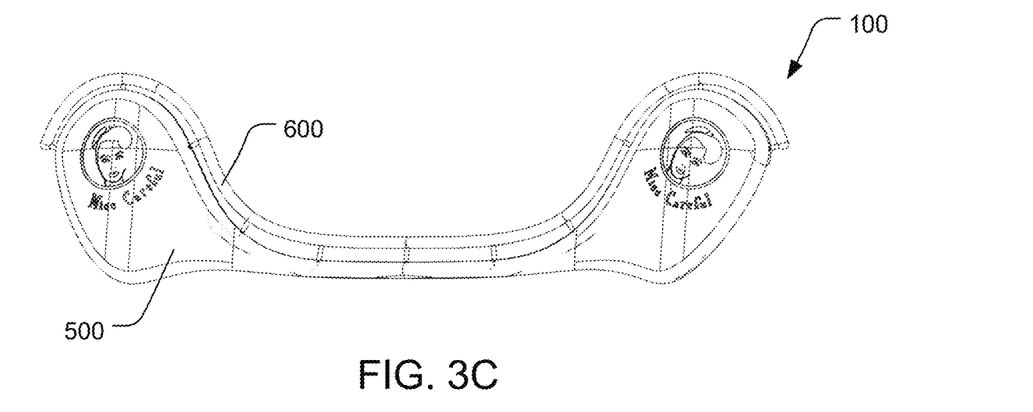
FIG. 3C is a front side elevation view of the ear guard assembly of the ear protection apparatus in accordance with one or more embodiments of the present invention.
Figure 3D:
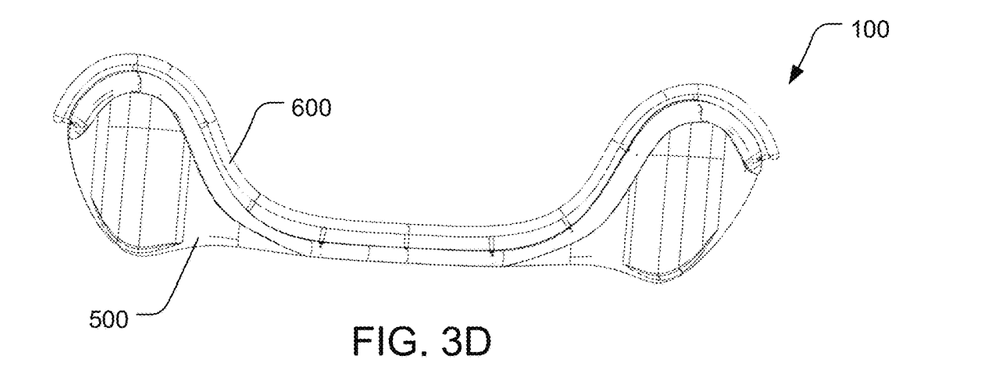
FIG. 3D is a back side elevation view of the ear guard assembly of the ear protection apparatus in accordance with one or more embodiments of the present invention.
Figure 3E:
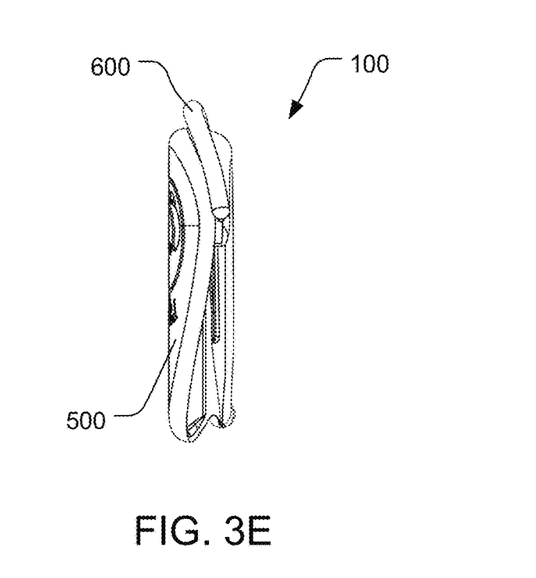
FIG. 3E is a left/right side elevation view of the ear guard assembly of the ear protection apparatus in accordance with one or more embodiments of the present invention.

FIG. 2 is an illustration of an ear cup 200 of the ear protection apparatus in accordance with one or more embodiments of the present invention. As illustrated, ear cup 200 comprises a housing 202 made of breathable material that is capable of absorbing moisture; an internal compartment 204 with soft inside lining; opening 210 to the internal compartment 204 having an elasticized band 206 for securely supporting the ear cup on the wearer's ear. In one or more embodiments, ear cup 200 is disposable and comprises fabric material.

FIGS. 3A-E are illustrations of different views of the ear guard assembly 100 of the ear protection apparatus 10 in accordance with one or more embodiments of the present invention. As illustrated, ear guard assembly 100 comprises a heat resilient protective band 500 coupled to a support assembly 600.

Figure 4A:
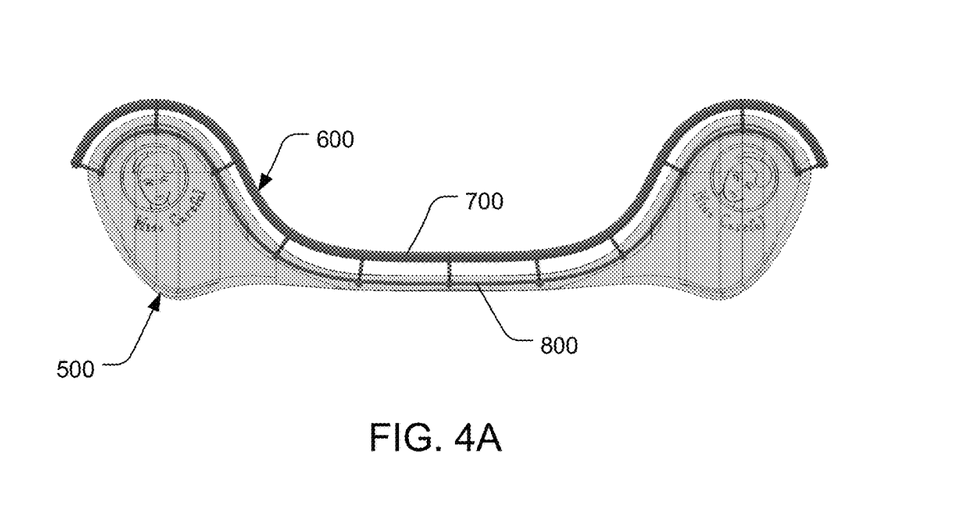
FIG. 4A is a shaded front side elevation view of the ear protection apparatus in accordance with one or more embodiments of the present invention.
Figure 4B:
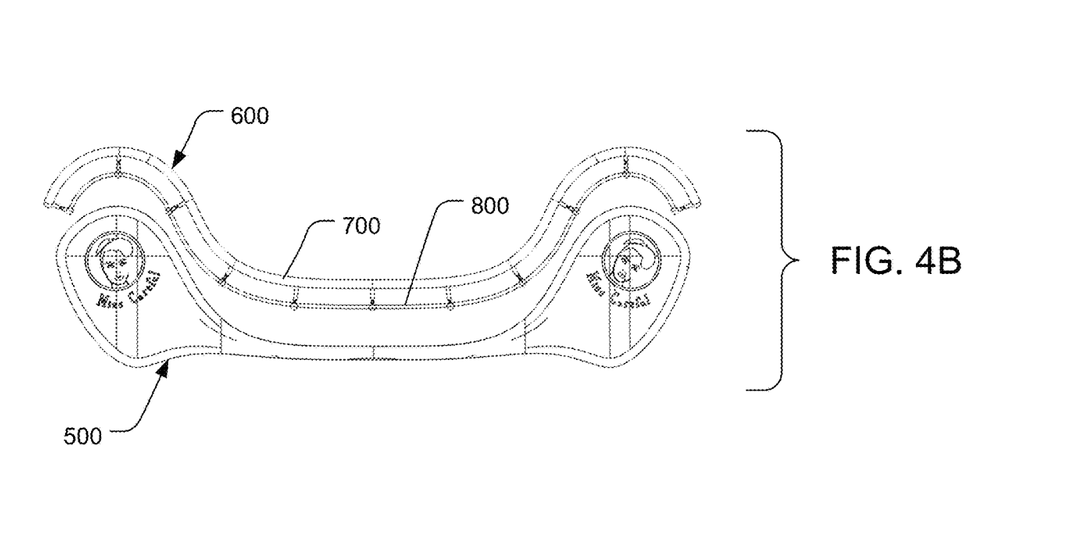
FIG. 4B is an exploded view of the ear protection apparatus in accordance with one or more embodiments of the present invention.
Figure 5A:
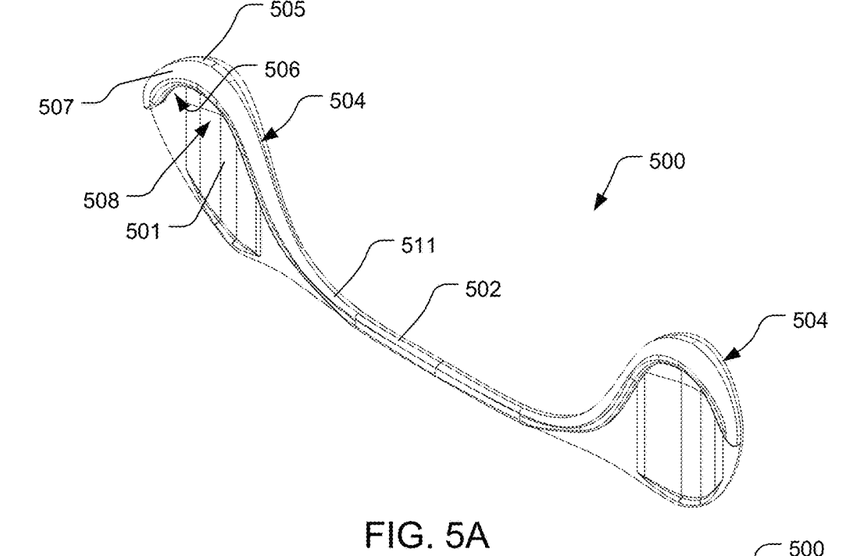
FIG. 5A is a perspective view from the back of the protective band of the ear protection apparatus in accordance with one or more embodiments of the present invention.
Figure 5B:
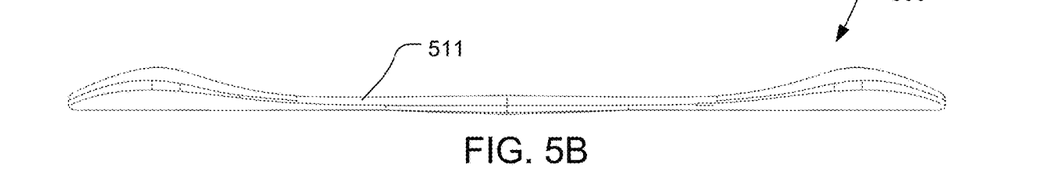
FIG. 5B is a top plan view of the protective band of the ear protection apparatus in accordance with one or more embodiments of the present invention.
Figure 5C:
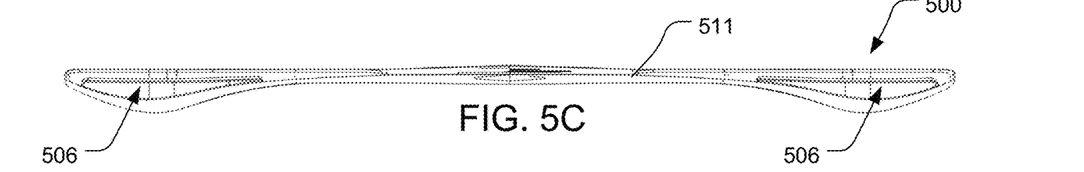
FIG. 5C is a bottom plan view of the protective band of the ear protection apparatus in accordance with one or more embodiments of the present invention.
Figure 5D:
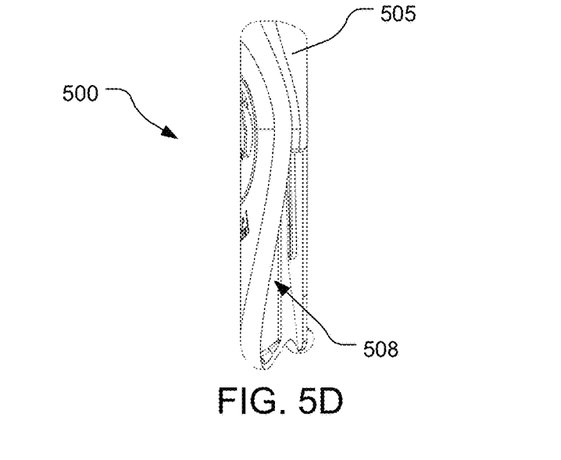
FIG. 5D is a left/right side elevation view of the protective band of the ear protection apparatus in accordance with one or more embodiments of the present invention.
Figure 5E:
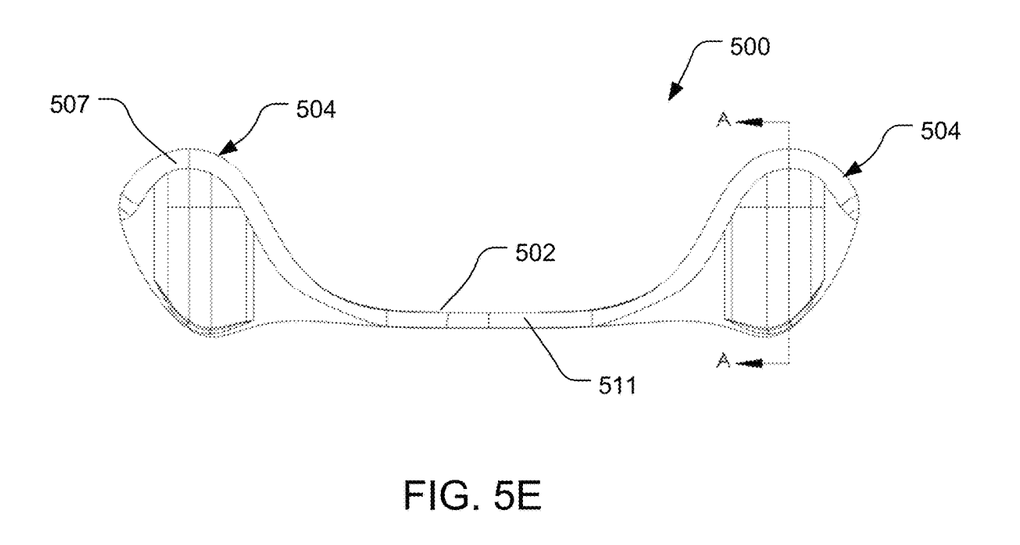
FIG. 5E is a back side elevation view of the protective band of the ear protection apparatus in accordance with one or more embodiments of the present invention.
Figure 5F:
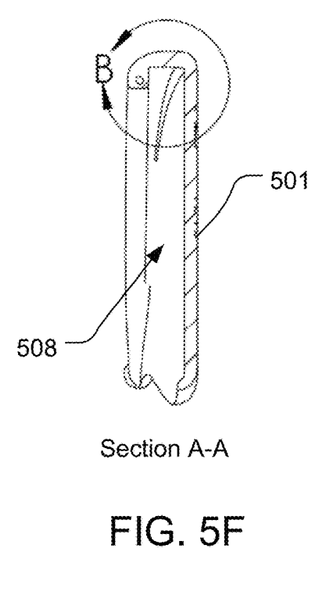
FIG. 5F is a cross-sectional view of section A-A of FIG. 5E in accordance with one or more embodiments of the present invention.
Figure 5G:
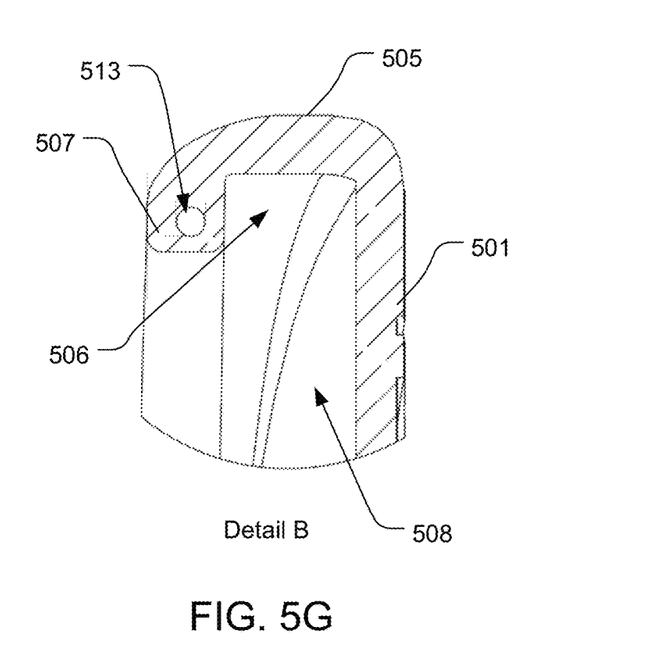
FIG. 5G is a detailed view of section B of FIG. 5F in accordance with one or more embodiments of the present invention.

FIG. 4A is a shaded view of the ear guard assembly 100 showing the integration of the support structure 600 with the protective band 500 of the ear protection apparatus 10 in accordance with one or more embodiments of the present invention. FIG. 4B is an exploded view of the ear guard assembly 100 showing the components of the support structure 600 with the protective band 500 of the ear protection apparatus 10 in accordance with one or more embodiments of the present invention. As illustrated in FIG. 4A, and described in more detail below, the wireframe 800 of the support structure 600 is coupled into the top section of protective band 500.

FIGS. 5A-G are illustrations of different views of the protective band 500 of the ear protection apparatus in accordance with one or more embodiments of the present invention. As illustrated, protective band 500 comprises a heat resilient connecting band 502 with an integrally formed ear protector 504 on each end of the support band. The connecting band 502 is configured to position each of the ear protectors 504 in contact with an ear of a user. The connecting band 502 is flexible and configured to be deformable (or bendable) so that it is foldable behind the user's neck or head such that each ear protector 504 houses one of the user's ear (see FIGS. 9A and 9B). In one or more embodiments, the protective band 500 comprises a single heat resilient material, e.g. silicone.

In one or more embodiments, each ear protector 504 comprises a frame that is sized and shaped to substantially cover each ear of the user. The frame comprises a sidewall 501, a top wall 505 and a skirt 507 that defines an inner cavity 508. Sidewall 501 extends upwardly from each end of connecting band 502, and terminates at a peripheral top wall 505. The peripheral top wall 505 extends inwardly and terminates in a downwardly extending skirt 507. The depth of the top wall 505 and height of the skirt 507 are configured to form a cup to securely and comfortably sit on top of a person's ear lobe. As illustrated, see FIG. 5E for example, skirt 507 extends and couples to one end of connecting band 502 thereby forming one continuous wall 511 for supporting the support assembly 600. The inner cavity 508 comprises a pocket 506 that is sized and shaped to slidably receive the user's ear in order to support the frame on top of the user's ear.

Figure 9A:
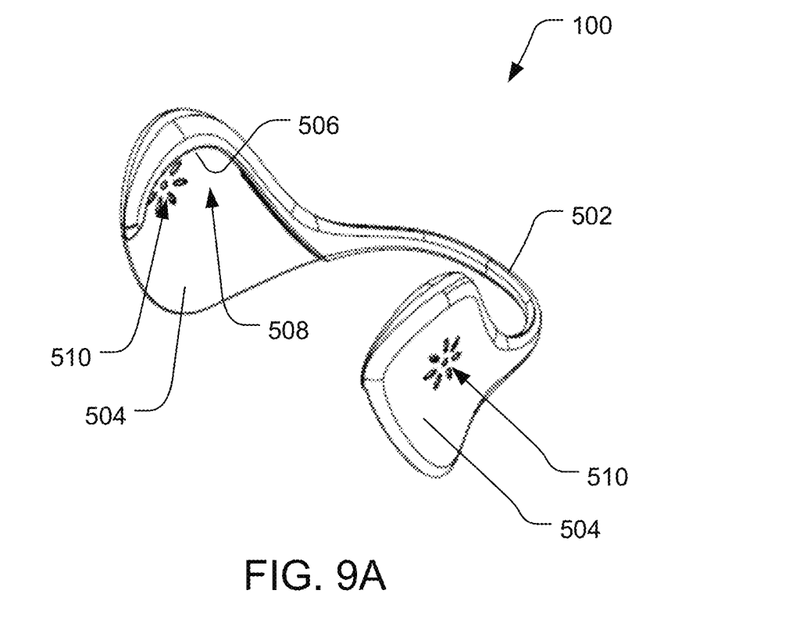
FIG. 9A is a perspective view of the protective band of the ear protection apparatus in a folded configuration in accordance with one or more embodiments of the present invention.
Figure 9B:
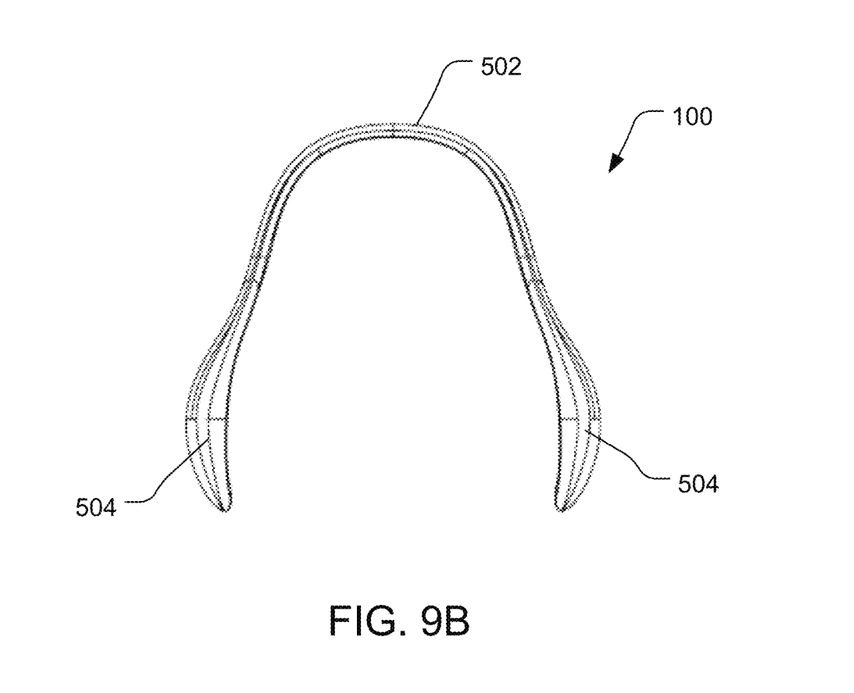
FIG. 9B is a top plan view of the protective band of the ear protection apparatus in a folded configuration in accordance with FIG. 9A.

In one or more embodiments, sidewall 501 includes at least one optional opening 510 to provide communication between the inner cavity 508 and the exterior of the ear protector, as illustrated in FIG. 9A.

Figure 6:
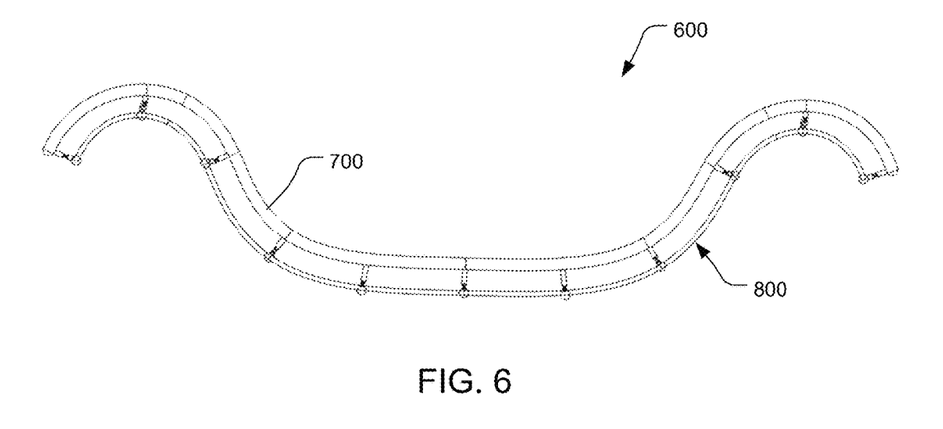
FIG. 6 is a side view of the support structure of the ear protection apparatus in accordance with one or more embodiments of the present invention.

In one or more embodiments, the ear guard assembly 100 includes a support structure 600 for maintaining the ear guard assembly 100 in a desired configuration around a person's head/neck. The support structure 600 couples to the protective band 500 at the continuous wall 511. FIG. 6 is a side view of the support structure 600 of the ear protection apparatus in accordance with one or more embodiments of the present invention. As illustrated, the support structure 600 comprises a support overmold 700 coupled to a metal wireframe 800. The metal wireframe could be steel or any other suitable metal. The support structure 600 spans length of the connecting band 502 and the length of the top of both ear protectors 504 to provide the desired stiffness for ear guard assembly 100. In one or more embodiments, the support overmold 700 comprises acrylic material. Those of skill in the art would appreciate that other materials, especially non-heat conducting types, may be used for the support overmold 700. In one or more embodiments, support structure 600 is removably coupleable to the protective band 500.

Figure 7A:
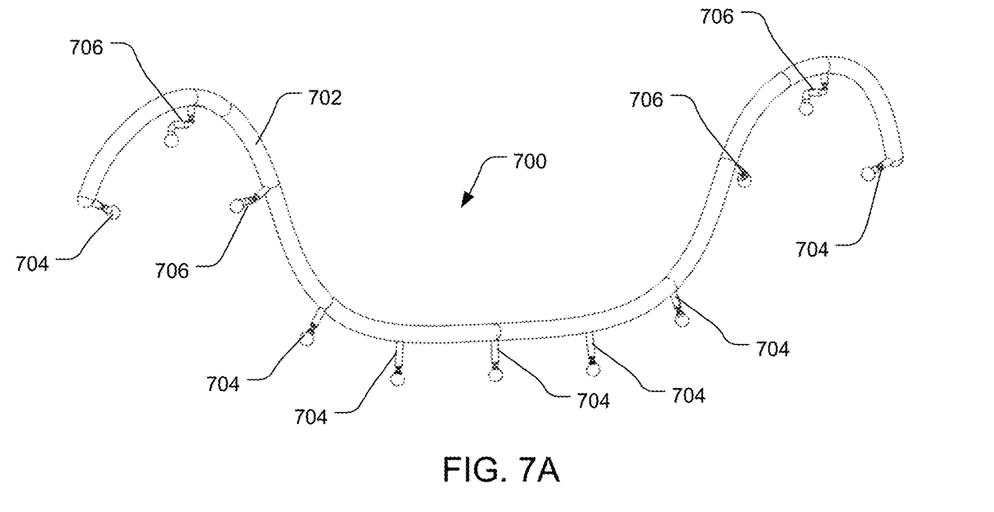
FIG. 7A is a side view of the support overmold of the ear protection apparatus in accordance with one or more embodiments of the present invention.
Figure 7B:
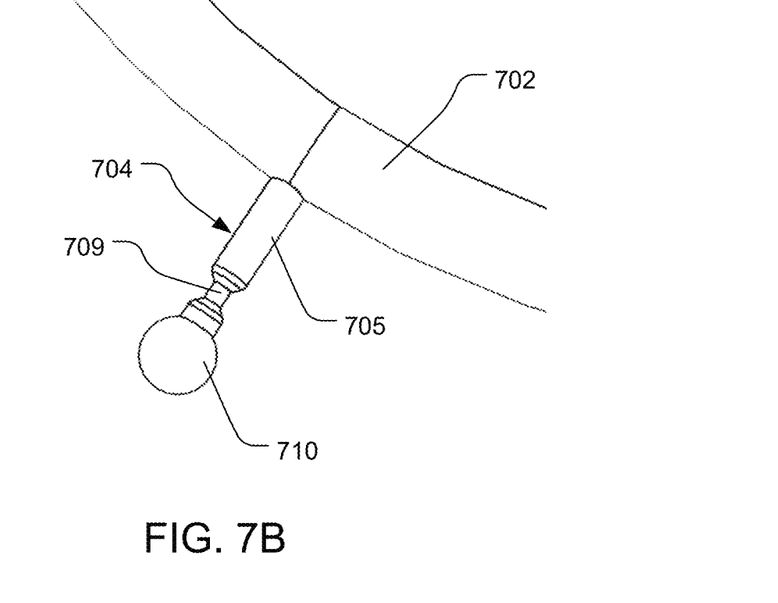
FIG. 7B is a close-up illustration of the linear leg in accordance with an embodiment of the present invention.

FIG. 7A is a side view of the support overmold 700 of the ear protection apparatus in accordance with one or more embodiments of the present invention. As illustrated, the support overmold comprises a body 702, a plurality of linear leg 704, and a plurality of angled leg 706.

In one or more embodiments, support body 702 comprises an overmold material, e.g. acrylic overmold. The plurality of linear leg 704 are arranged as follows: one at each end of the support body 702 of support overmold 700, and at least one in the middle section of the support body 702 where the support structure 600 couples to the connecting band 502 section of the continuous wall 511. As better illustrated in FIG. 7B, each of the plurality of linear leg 704 comprises a vertical rod 705 coupled at one end to the support body 702 and a second end to a foot coupler 710 through a flexible joint 709. The leg structure with a flexible joint makes it possible to operationally configure the ear guard assembly 100 to a desired shape around the user's head/neck.

Figure 7C:
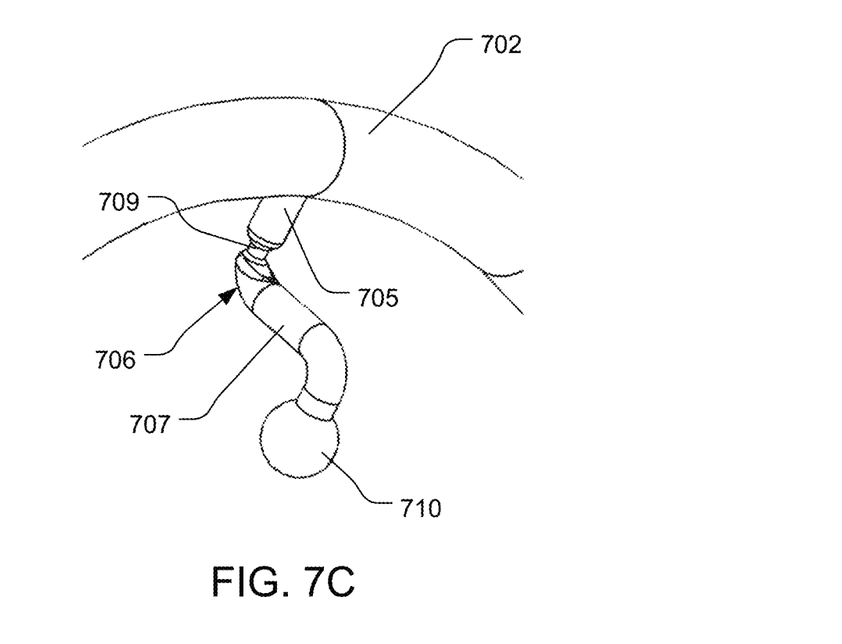
FIG. 7C is a close-up illustration of the angled leg in accordance with an embodiment of the present invention.

FIG. 7C is a close-up illustration of the angled leg 706 in accordance with an embodiment of the present invention. As illustrated, each one of the plurality of angled leg 706 comprises a vertical rod 705 coupled at one end to the support body 702 and a second end to a horizontal rod 707 through a flexible joint 709. The horizontal rod 707 is then coupled to foot coupler 710. One or more of the angled leg 706 is coupled to the support body 702 where the support structure 600 couples to the two sections of skirt 507 of the continuous wall 511.

Figure 8:
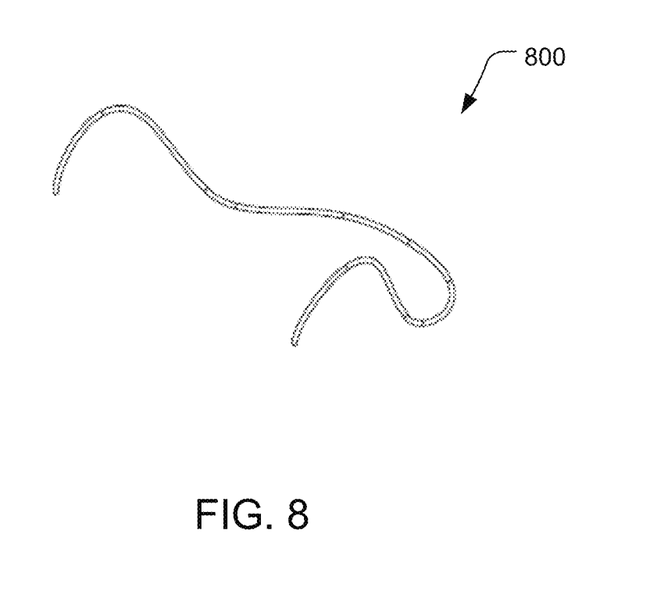
FIG. 8 is a perspective view of the wireframe of the support structure of the ear protection apparatus in accordance with one or more embodiments of the present invention.

FIG. 8 is a perspective view of wireframe 800 of the support structure 600 of the ear protection apparatus in accordance with one or more embodiments of the present invention. As illustrated, in one or more embodiments, the wireframe comprises a spring steel wire insert that resides inside the continuous band 511 and coupled to the feet of the overmold 700. The wireframe 800 spans the connecting band 502 and the skirt 507 of both ear protector 504 of the protective band thus providing stiffness.

In one or more embodiments, the wireframe 800 is coupled to the support overmold via the plurality of foot coupler 710 in orifice 513 (see FIG. 5G), which runs the length of the continuous wall 511. Each foot coupler 710 may be configured with an orifice (not shown), for example, for coupling the wireframe.

Figure 10:
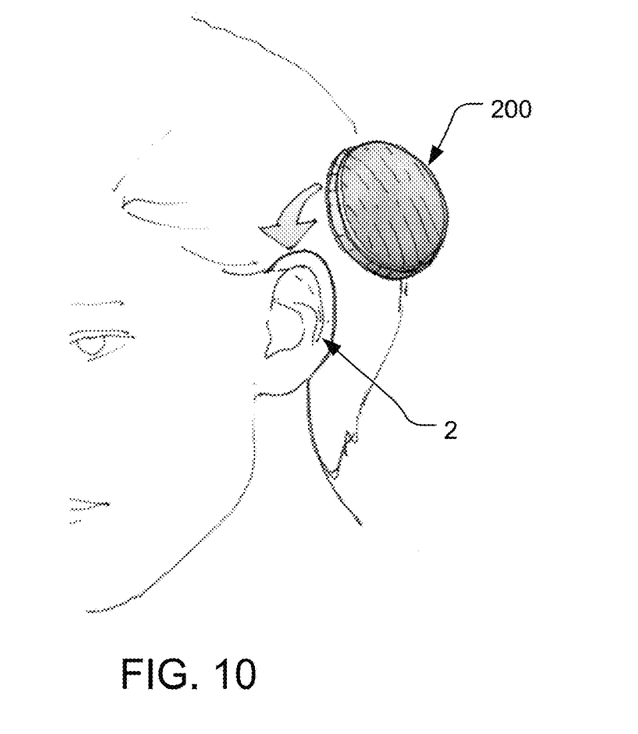
FIG. 10 is an illustration of application of the ear cup of the ear protection apparatus over a wearer's ear.

FIG. 10 is an illustration of application of the ear cup 200 of the ear protection apparatus over a user's ear 2. In use, ear cup 200 is applied over the user's ear by stretching the elastic band over the ear. The protective band 500 is then applied by hooking the pockets 506 of the ear protector over the ear cup, e.g. 200, as illustrated in FIG. 11, or directly over the ear lobe on both ears.

In one or more embodiments, the protective band 500 may be configured to provide additional protection for area of the cheeks near the ear, and the skin and neck areas behind the ears. In such configuration, the ear protector 504 may be configured with enough coverage area around the desired area around the ear to provide the desired protection.

In one or more embodiments, the connecting band 502 may be configured to provide protection for the user's neck. In such configuration, the band may be shaped like a wide belt to provide enough surface area of protection for the neck. (See FIG. 11).

While the invention herein disclosed has been described by means of specific embodiments and applications thereof, numerous modifications and variations could be made thereto by those skilled in the art without departing from the scope of the invention set forth in the claims.

What is claimed is:

1. An apparatus for protecting the ears of a human during hair styling comprising:
    an ear guard structure comprising a first ear protector coupled to a second ear protector by a connecting band, wherein the connecting band is configured to position each of the first ear protector and the second ear protector in contact with a user's ear, wherein the connecting band is further configured to be foldable behind the user's neck, wherein each of first ear protector and the second the ear protector comprises a frame that is sized and shaped to substantially cover the ear of the user, wherein the frame comprises an outer shell that defines an inner cavity comprising a pocket that is sized and shaped to be slidably received over the user's ear to support the frame on top of the user's ear; and
    a support structure coupled to the top of the ear guard structure, wherein the support structure is configured to be deformable to a shape around the back of the user's neck or head, wherein the support structure comprises a metal wireframe running a length of an orifice beginning from a topside of the first ear protector and through the connecting band to a topside of the second ear protector, wherein the support structure further comprises an acrylic overmold external to the ear guard structure wherein the acrylic overmold is coupled to the wireframe via a plurality of foot couplers with legs along said wireframe's length.

2. The apparatus of claim 1, wherein the ear guard structure comprises heat resilient material.

3. The apparatus of claim 1, wherein the ear guard structure comprises silicon material.

4. The apparatus of claim 1, wherein the wireframe is a steel wireframe.

5. The apparatus of claim 1, wherein the outer shell further includes at least one opening to provide communication between the inner cavity and the exterior of the ear protector.

6. The apparatus of claim 1, further comprising an ear cup having a substantially concave shape to fit around the user's ear and configured to fit inside the inner cavity, wherein the ear cup is formed of a breathable fabric material.

* * * * *